United States Patent [19]

Inouye et al.

[11] Patent Number: 5,320,958
[45] Date of Patent: Jun. 14, 1994

[54] ISOLATED BACTERIAL REVERSE TRANSCRIPTASE

[75] Inventors: Sumiko Inouye, Bridgewater; Mei-Yin Hsu, North Plainfield; Susan Eagle, South Amboy; Masayori Inouye, Bridgewater, all of N.J.

[73] Assignee: University of Medicine and Dentistry of New Jersey, Newark, N.J.

[21] Appl. No.: 315,316

[22] Filed: Feb. 24, 1989

[51] Int. Cl.$^5$ .......................... C12N 9/12; C12N 1/12; C12N 1/00; C12N 15/54
[52] U.S. Cl. ................................. 435/194; 435/822; 435/252.1; 935/14
[58] Field of Search ............ 435/193, 194, 822, 252.1; 935/14, 18

[56] References Cited

PUBLICATIONS

Dhundale et al, *Structure of Ms DNA from My...*, Cell, vol. 51, 1105–1112, 1987.
Dhundale et al, *Mutations That Affect Production...*, J. of Bacteriology, vol. 170, No. 12, 5620–5624, 1988.
Furuichi et al., Cell, 48, 47–53 (1987), "Branched RNA Covalently Linked to the 5' End of a Single-Stranded DNA in Stigmatella aurantiaca: Structure of msDNA".
Furuichi et al., Cell, 48, 55–62 (1987), "Biosynthesis and Structure of Stable Branched RNA Covalently Linked to the 5' End of Multicopy Single-Stranded DNA of Stigmatella aurantiaca".

*Primary Examiner*—Douglas W. Robinson
*Assistant Examiner*—Michael V. Meller
*Attorney, Agent, or Firm*—Weiser & Associates

[57] ABSTRACT

The present invention relates to an isolated bacterial reverse transcriptase. The reverse transcriptase synthesizes a peculiar RNA-DNA complex called msDNA which is a single-stranded DNA structure branched out from an RNA molecule. The gene coding for the reverse transcriptase has been isolated and sequenced. It codes for a polypeptide of 485 amino acid residues. This is the first time that a reverse transcriptase has been found, identified and isolated from a prokaryotic microorganism of which the amino acid sequence is shown in FIGS. 2a–2d.

2 Claims, 9 Drawing Sheets

FIG. 2A

```
     TCA TCC GCG AGA CGC GCT CCT ACG CGG GCC AGA CGG    60
     TGT ACC GGG TTT CCC TGG ATG GTC AGG TGG CGG AGT GGG GCC GCA CGG GCT   120
     CGC CGC CTC ACC AGC GGC TCT GGT TCG ACT CGG AAG CGC GGG GAG CGT ACT TCG   180
     CGC GCC CTC AGA AGT TGG CGG CTG ACG GCT ACA TCG CGG CCT CGG CAT TGG TGT AAA   240
     CCC TTC AAC CAC GGC TCG CGC CGC GCC GGC CAG GAC AGG TGC GAC GAA GAG ACG   300

ACG ACG TGC GCT TCA CGC CGC AGC CGA AGC TCC GGA GTG CAT CAG CCT GAG CGC   360
     TGC TGC ACG AGT GCG CGC TCG CCG CGC AGT GCG CTC TCC AGG CCT CAC GTA GTC GGA CTC GCG
                                      a₂ →    ⇨RNA
     CTC GAG CGG CGG AGC GGC GTT GGG CAA CGC CCG CTC CGG TTG GAA TGC AGG ACA CTC TCC GGA AGG   420
     GAG CTC GCC GCC TCG CCG CGC AGT GCG CTC TCC AGG CCT CAC GTA GTC CGG AGG CCT TCC
     TAG CCT GTT CTT GGC TCT CTC CCT AGG CAC TAC GGC CAG GGT GGG TAG CGG AGC CAA   480
     ATC GGA CAA GAA CCG AGA GAG GGA TCC GTG ATG CCG GTC CCA CCC ATC GCC TCG GTT
     CGA CGC GAC CGC CGT TTA CCC ACC CGG GCG GTA GTG CCT AGG AGG GGA GAG CCG GTG AGG   540
     GCT GCG CTG GCG AAT GGG TGG CGG CAT CAC CGG AGG TCC TCC CCT CTC GGC CAC TCC
     CTA CCG TGC CCC AGG TAA GAT GGT GCT GGT GTT CCG GCC TCC CGG CCG GAG CGC CAT   600
     GAT GGC ACG GGG TCC ATT CTA CCA CGA CCA CAA GGC CGG AGG CTG ACG AGC GCG GTA
                                ⇨DNA                                        a₁ →
```

FIG. 2B

```
GTC CCG TCT TCC ATC GCC GCG CAA GGT GCA GAC ATG ACC GCC AGG CTG GAC CCG 660
 V   P   S   S   I   A   A   Q   G   A   D   M   T   A   R   L   D   P
                     AluI▼
TTC GTC CCC GCA GCT TCG CCC CAG GCC GCC GTG CCC ACG CCC GAG CTC ACC CCG TCG TCA 720
 F   V   P   A   A   S   P   Q   A   A   V   P   T   P   E   L   T   P   S   S
GAC GCG GCC GCG AAG CGT GAA GCC GCC CGG CGG ACG CAC GCC CTC GCC GAA GCG 780
 D   A   A   A   K   R   E   A   A   R   R   T   H   A   L   A   E   A
AAG GCC ATC GAC GAA GCC GGG GGC GGC CTC GTG CAG GTG CAG CAG GCG CCG 840
 K   A   I   D   E   A   G   G   G   L   V   Q   V   Q   Q   A   P
        *50
GGC CTC GCG GTG GAG GAC CTG GAC TTC TCC AGC GCC TCC GTC TCC CGC GCG 900
 G   L   A   V   E   D   L   D   F   S   S   A   S   V   S   R   A
AAG GAG AAG AAG AAG GCC GAG GCC ACC GAG CGG CGC GCG CTG AAG CGT CAG GCG CAC GAG 960
 K   E   K   K   K   A   E   A   T   E   R   R   A   L   K   R   Q   A   H   E
                                                  *100
GCG CTC GCG GTG AAG GCC ACG CAC GTG GGC CTG GGC GCA GGC GTG CAC TGG GCG GAG GAC CGC 1020
 A   L   A   V   K   A   T   H   V   G   L   G   A   G   V   H   W   A   E   D   R
                                                           SmaI▼
GCG TGG AAG GCC GCG TTC GAC GTG CCC CAC CCC CAC CGC CCC AAC GCC CGG GCC AAC GGC CTG ACG 1080
 A   W   K   A   A   F   D   V   P   H   P   H   R   P   N   A   R   A   N   G   L   T
CTG GCC GAC TCG GCC GAG GCG GCC CTG GCC AAG CTG GGG AGC GTG TCC AAG CTG CGC 1140
 L   A   D   S   A   E   A   A   L   A   K   L   G   S   V   S   K   L   R
     *150
GAG CTC GAC GCC GAG GCC GTC CAC CGG GAG GTG GCC CTG GCC AAG ACG GCC ACG CAC TAC GTG AGC TGG ACG ATT CCG 1200
 E   L   D   A   E   A   V   H   R   E   V   A   L   A   K   T   A   T   H   Y   V   S   W   T   I   P
TGG TTC GCG TTC CAC CGC GAG
 W   F   A   F   H   R   E
```

FIG. 2C

```
AAG CGG GAC GGC AGC AAG CGC ACG ATT ACG TCC CCC AAG CCT GAG CTG AAG GCA GCG CAG 1260
 K   R   D   G   S   K   R   T   I   T   S   P   K   P   E   L   K   A   A   Q

CGC TGG CTG CTC TCC AAC GTC GTG GAG AAC GCG CTG CCG CGG CAC GTG CAC CAC GGC TTC 1320
 R   W   L   S   N   V   V   E   N   A   L   P   R   H   V   H   H   G   F
                                              *200

GTG GCG GGA CGC TCC ATC CTC ACC AAC GCC CTG GCC CAC CAG CAG GAC GTG GCG GTG GTG 1380
 V   A   G   R   S   I   L   T   N   A   L   A   H   Q   Q   D   V   A   V   V

AAG GTG GAC CTC AAG GAC TTC TTC CCG TCC ACC CTG TGG CGC GTG AAG GGC CTG TTG 1440
 K   V   D   L   K   D   F   F   P   S   T   L   W   R   V   K   G   L   L
        *250

CGG AAG GGC GGC CTG CGG CGG GAG GGC ACG TCC TCC ACG CTG CTC TCG CTC TCC ACG GAA GCG 1500
 R   K   G   G   L   R   R   E   G   T   S   S   T   L   L   S   L   S   T   E   A

CCG CGG GAG GCC GTG GCG CAG TTC CGG GGC AAG CTG CAC GTG AAG GGC CCG CGG GCG 1560
 P   R   E   A   V   A   Q   F   R   G   K   L   H   V   K   G   P   R   A
                                                      *300

CTG CCC CAG CTG TCC GCG CTC GCG AAG TCG CCG ATC ACC AAC GCG CTG TGC CTG AAG CTG GAC 1620
 L   P   Q   L   S   A   L   A   K   S   P   I   T   N   A   L   C   L   K   L   D

AAG CGG CTG TCC GCG CTC GCG AAG CGG CGC AAG GCG TAC ACG CGC TAC GCG GAC GAC 1680
 K   R   L   S   A   L   A   K   R   R   K   A   Y   T   R   Y   A   D   D

CTG ACC TTC TCG TGG ACG AAG GCG AAG CAG CCC AAG CAG ACG CCG CGG CAG CGT CCC CCG 1740
 L   T   F   S   W   T   K   A   K   Q   P   K   Q   T   P   R   Q   R   P   P
        *350

GTG GCG GTG CTG CTG TCT CGC GTG CAG GAA GTG GTG CAG GAG GCC GAG GGC TTC CGC CAC 1800
 V   A   V   L   L   S   R   V   Q   E   V   V   Q   E   A   E   G   F   R   H

CCG GAC AAG ACG CGC GTG GCG CGC AAG CGC ACC GGC AAG CAG CGG GTG ACG GGG CTG GTC GTG 1860
 P   D   K   T   R   V   A   R   K   R   T   G   K   Q   R   V   T   G   L   V   V
                        *400
```

FIG. 2D

```
        AAT GCG GCG GGC AAG GAC GCG CCG GCC CGA GTC CCG CGC GAC GTG GTG CGC CAG CTC 1920
N        N   A   A   G   K   D   A   P   A   R   V   P   R   D   V   V   R   Q   L

CGC GCC ATC CAC AAC CGG AAG AAG GGC AAG ATG ACG CCG GGC GAG GAG GGC GAG TCG CTG GAG 1980
R   A   I   H   N   R   K   K   G   K   M   T   P   G   R   E   E   G   E   S   L   E

CAG CTC AAG GGC ATG GCC TTC ATC CAC ATG ACG GAC CCG AAG GCC CGC GCC TTC 2040
Q   L   K   G   M   A   F   I   H   M   T   D   P   K   A   R   A   F
     *450

CTG GCT CAG CTC ACG GAG CTG GAG TCC ACG AGC GCG GCT CCG CAG GCG GAG TGA CGC 2100
L   A   Q   L   T   E   L   E   S   T   A   S   A   A   P   Q   A   E   -

TCA GCG CGC GTC CGT CGC CGA GGT GCC GCC GCG CGC CAG CAA CGC GGC ATT GAG GAA GTC CGT 2160

CAG CCG GCG CGG GTA C
```

FIG. 3

| | | |
|---|---|---|
| HIV | RT | VKLKPGMDGPKVKQ WPLTEEKIKALVEICTEMEKEGKISKIGPENPYNTPVFAIKKKDSTKWR |
| HTLV1 | RT | RPWARTPPKAPRNQ PVPFKPERLQALQHLVRKALEAGHIEPYTG PGNNPVFPVKKA NGTWR |
| Ec-67 | RT | NVLYRIGSDNQYTQFTIPKKGKGVRTISAPTDRL KDIQRRICDLLSDCRDEIFAIRKI SNNYS |
| Mx-162 | RT | AFHREVDTATHYVSWTIPKRDGSKRTITSPKPEL KAAQR WVLS NVV ERLP VHGAA |
| | | o oooo o o oo x o |

| | | | |
|---|---|---|---|
| HIV | RT | KLVDFRELNKRTQDFWEVQLGIPHPAGLKKK KSVTVLDVGDAYFSVPLDEDFRKYT | A |
| HTLV1 | RT | FIHDLRATNSLTIDLSSSSPGPPDLSSLPTTLAHLQTIDLRDAFFQIPLPKQFQPYF | A |
| Ec-67 | RT | FGFE RGKSIILNAYKHRGKQIILNIDLKDFFESFNFGRVRG YFLS NQDF | L |
| Mx-162 | RT | HGFV AGRSILTNALAHQGADVVVKVDLKDFFPSVTWRRVKGLLRKGGLREGTSTLLSLLSTEAP | |
| | | oo o o oo o xx o o °°°°° o xxx o o x x | |

| | | |
|---|---|---|
| HIV | RT | FTIP SINNETPGIRYQYNVLPQGWKGSPAIFQS SMTKILEPFKKQNPDIVIYQYMDDLYVG |
| HTLV1 | RT | FTVP QQCNYGPGTRYAWKVLPQGFKNSPTLFEM QLAHILQPIRQAFPQCTILQYMDDILLA |
| Ec-67 | RT | LN PVVATTLAKAACYN GTLPQGSPCSPIISNLICNIMDMRLAKLAKKY GCTYSRYADDITI |
| Mx-162 | RT | REAVQFRGKLLHVAKGP RALPQGAPTSPGITNALCLKLDKRLSALAKRL GFTYTRYADDLTF |
| | | o o •••• o •• o oo o ooo o x o°° ooo oo o ••ooo••• x |

| | | |
|---|---|---|
| HIV | RT | S DLEIGQHRTKIEELRQHLLRWGLTTP DKKHQKEP PFLWMGYELHPDKWTVQPIVLPE KD |
| HTLV1 | RT | S PSHEDLLLLSEATMASLISHGLPVS ENKTQQTPGTIKFLGQIISPNHLTYDAVPTVPI RS |
| Ec-67 | RT | STNKNTFPLEMATVQPEGVVLGKVLVKEIENSGFEINDSKITRLTYKTSRQEVT GLTVNRIVNID |
| Mx-162 | RT | SWTKAKQPKPRRTQRPPVAVLLSRVQEVVEAEGFRVHPDKTRVARKGTRQRVT GLVVNAAGKDA |
| | | • o o o oo oo o oX o ooo o oo o• oo oo oo°° xx |

| | | |
|---|---|---|
| HIV | RT | SWTVNDIQKLVGKLNWASQIYP |
| HTLV1 | RT | RWALPELQALLGEIQWVSKGTP |
| Ec-67 | RT | RCYYKKTRALAHALYRTGE YK |
| Mx-162 | RT | PAARVPRDVVRQLRAAIHN RK |
| | | x o |

FIG. 4A

```
Mx-162   18  PTPELTAPSSDAAAKREARRLAHEALLVRAKAIDEAGGADDWVQAQLVSKGLAVEDLD-FSSASEKDKKA-WKEKK    91
                 o o  o                                    o         o       o  oo
Mo-MLV 1070  PDPDMTRVTNSPSLQAHLQALYLVQHEVW-RPL-AAAYQEQ-LDRPVVPHPYRVGDTVWRRHQTKNLEPRWKGPY  1142
             ooo   o                          o                  o       o       oo Mx 162   92  KAEATERRALKRQAHEAW-KATHVGHLGAGVHWAEDRL   128
                        o   ooo
Mo-MLV 1143  TVLLTTPTALKVDGIAAWIHAAHVKAADPGGG-PSSRL   1179
                o        ooo     oo o  oo         oo
```

FIG. 4B

```
Mx-162  411  GKDAPAARVPRDVVRQLRAAIHNRKKGKPGREGESLEQLKGMAAFIHMTD-PAKGRAF-LAQLTELESTASAAPQAE   485
                               o                o           oo     oo  o        oo       oo
HIV     396  GKEGHSARQCR-APR--RQGC--WKCGKPGHIMTNCPD-R-QAGFLGLGPWGKKPRNFPVAQVPQ-GLTPTAPP     461
             oo         o  o  o  o  o oooo                o o                         o o
```

FIG. 5A

```
Mx-162       304 GP-RALPQGAPTSPGITNALCLKLDKRLSALAKRL-GFTYTRYADDLTF-SWTKAKQPKPRRTQRPPVAVL  371
                                                    oooo         o                         
Ec-67        159 YN-GTLPQGSPCSPIISNLICNIMDMRLAKLAKKY-GCTYSRYADDITI-STNKNTFPLEMATVQPEGVVL  226
                 oooo  oo                            oo ooo oooo  o                         
Ec-86        130 YK-NLLPQGAPSSPKLANLICSKLDYRIQGYAGSR-GLIYTRYADDLTL-SAQSMKKVVKARDFLFSIIPS  197
                 oooooo oo                           o  ooooooooo  o                         
HIV          311 YQYNVLPQGWKGSPAIFQS---SMTKILEPFKKQNPDIVIYQYMDDLYVGS-DLEIGQHRTKIEELRQHLL  377
                 oooo     oo            oo               o ooo      o                       
HTLV1        150 YAWKVLPQGFKNSPTLFEM---QLAHILQPIRQAFPQCTILQVMDDILLAS---PSHEDLLLLSEATMASLI 215
                 oooo    oo               o              o ooo                              
Mo-MLV       303 LTWTRLPQGFKNSPTLFDE---ALHRDLADFRIQHPDLILLQYVDDLLLAA-TSELDCQQG-TRALL-QTL  367
                 oooo    oo                               o ooo       o          o          
RSV          141 FQWKVLPQGMTCSPTICQL---VVGQVLEPLRLKHPSLCMLHVMDDILLAA---SSHDGLEAAGEEVI-STL 205
                 oooo    oo                                ooo                     o        
BLV          122 FAWRVLPQGFINSPALFER---ALQEPLRQVSAAFSQSLLVSYMDDILYAS---PTEEQRSQCYQALA-ARL 186
                 o oo    oo                               o ooo                    o        
Mt.plasmid   288 IATNGVPQGASTSCGLATYNVL------ELFLRY--DELIMYADDGIL-CRQDPSTPDFSVEEAGVVQEP  348
                 oooo   oo                              oooo       o                        
17.6         339 YEYLRMPFGLKNAP-ATFQRCMN-DI-----LRPLLNKHC-LVYLDDIIVFS-TSLDEHLQSLGLVFE--KL 399
                      o  o oo    oo                         oo oo    o                      
GYPSY        284 YEFCRLPFGLRNASSIFQR---ALDDV-----LREQI-GKICYVVVDDVIIFS---ENESDHVRHIDTVLK-CL 344
                    o  oo oo     oo                        oo oo                            
Copia       1032 CKLNKAIYGLKQAARCWFR--CIYI---LDKGNINENIYV-LLYVDDVVIAT---GDMTRMNNFKRYLME-KF 1112
                                    oo                      oo ooo                          
Tal-3        990 CLLKKSLYGLKQSPRQWNA--CVYV-KQVSE-QEHLYL----LLYVDDMLIAG---KSKSEINKVKEQLSM-EF 1069
                       o   oo    oo  oo                     oo ooo      o                   
Ty912        948 IRLKKSLYELKQS-GANWYE--EVRG-WSCVFKNSQV-TICLFVDDMVLFS---KNLNSNKRIIEKLKM-QY 1023
                       o   oo   o                         oo oo       o                     
```

ISOLATED BACTERIAL REVERSE TRANSCRIPTASE

This patent application is related to two patent applications co-filed on the same date identified as THE USE OF REVERSE TRANSCRIPTASE TO SYNTHESIZE BRANCHED-RNAS LINKED MULTICOPY SINGLE-STRANDED DNA, Lampson et al., Ref.: 377.5019P and REVERSE TRANSCRIPTASE FROM *ESCHERICHIA COLI*, Lampson et al, Ref.: 377.5021P, and having Ser. Nos. 07/315,427 and 07/315,432, respectively which are incorporated herein by reference.

SUMMARY OF THE INVENTION

In accordance with the invention, Myxobacteria have been shown to produce a peculiar RNA-DNA complex called msDNA, in which a single-stranded DNA is branched out from a RNA molecule (msdRNA) by a 2',5' phosphodiester linkage. It has been predicted that reverse transcriptase is required for msDNA biosynthesis. In accordance with the invention, the gene for reverse transcriptase is identified in *Myxococcus xanthus* in the region which has been demonstrated to code for a cis- or trans-acting element for msDNA synthesis. This gene is located immediately downstream of the msdRNA coding region, and codes for a polypeptide of 485 amino acid residues. The polypeptide shows sequence similarity with retroviral reverse transcriptases. This fact together with the mode of msDNA synthesis suggests a possible relationship between retroviruses and the msDNA system. Analysis of the gene and the distribution of the msDNA system in independent isolates of *M. xanthus* indicates that the element is as old as other essential genes in *M. xanthus* and that it was not recently acquired into the genome.

BACKGROUND OF THE INVENTION

The existence of a peculiar branched RNA-linked DNA molecule called msDNA (multicopy single-stranded) has been demonstrated in various myxobacteria, Gram-negative soil bacteria (Yee et al., 1984; Dhundale et al., 1985; Furuichi et al., 1987; Dhundale et al., 1987; Dhundale et al. 1988 *J. Biol. Chem.* 48, 47–53 and 55–62. msDNA (msDNA-Mx162) from *Myxococcus xanthus* consists of 162-base single stranded DNA, the 5' end of which is linked to the 2' position of the 20th rG residue of a 77-base RNA molecule (msdRNA) by a 2', 5'- phosphodiester linkage (Dhundale et al., 1987). It exists at a level of approximately 700 copies per genome. *Stigmatella aurantiaca* also possesses an msDNA (msDNA-Sa163) which is highly homologous to msDNA-Mx162 (Furuichi et al., 1987). In addition to msDNA-Mx162, *M. xanthus* has another smaller species of msDNA (mrDNA or msDNA-Mx65), which has no primary sequence homology with msDNA-Mx162 or msDNA-Sa163 (Dhundale et al., 1988 *J. Biol. Chem.*). However, all msDNAs so far characterized share key structural features such as a branched rG residue, stem-and-loop structures in RNA and DNA molecules, and a DNA-RNA hybrid at the 3' ends of DNA and RNA molecules.

Previously it was predicted that reverse transcriptase is required for msDNA biosynthesis on the basis of the finding that msdRNA is derived from a much longer precursor, which can form a very stable stem-and-loop structure (Dhundale et al., 1987). This precursor molecule was proposed to serve as a primer for initiating msDNA synthesis as well as a template to form the branched RNA-linked-msDNA. The latter reaction requires reverse transcriptase activity. In *M. xanthus*, the region coding for the RNA molecule (msr) is located on the chromosome in the opposite orientation to the msDNA coding region (msd) with the 3' ends overlapping by 6 bases for msDNA-Mx65 (Dhundale et al., 1988 *J. Biol. Chem.*) or by 8 bases for msDNA-Mx162 (Dhundale et al., 1987). In addition, as in all the msDNAs found in myxobacteria, there is an inverted repeat comprised of a 14-base sequence for msDNA-Mx65 (Dhundale et al., 1988 *J. Biol. Chem.*) or a 34-base sequence for msDNA-Mx162 (Dhundale et al., 1987) and a 33-base sequence for msDNA-Sa163 (Furuichi et al., 1987) immediately upstream of the branched G residue and a sequence immediately upstream of the msDNA coding region. As a result of this inverted repeat, a longer primary transcript beginning upstream of the RNA coding region and extending through the msDNA coding region is considered to self-anneal and form a stable secondary structure. When three base mismatches were introduced into the secondary structure immediately upstream of the branched rG residue, msDNA synthesis was almost completely blocked. However, if three additional base substitutions were made on the other strand to resume the complementary base pairing, msDNA production was restored (Hsu et al., 1989). This result strongly supports the proposed model for msDNA synthesis.

It has also been shown that a deletion mutation at the region 100 base pairs (bp) upstream of the DNA coding region (msd) and an insertion mutation at a site 500 bp upstream of msd caused a significant reduction in msDNA production (Dhundale et al., 1988 *J. Bacteriol.*). This indicates that there is a cis- or trans-acting positive element required for msDNA synthesis in this region. In this report we determined the DNA sequence of this region and found an open reading frame (ORF) of 485 amino acid residues beginning with an initiation codon, ATG, which is located 77 bp upstream of msd (or 231 bp downstream of msr). The very close proximity between msd and the ORF suggests that they may be transcribed as a single transcript. The amino acid sequence of the ORF shows similarity with retroviral reverse transcriptases. A possible origin of the reverse transcriptase gene as well as a possible relationship between the msDNA system and retroviruses is discussed herein. Recently, some strains of *Escherichia coli* were found to produce msDNA and the gene for reverse transcriptase which is essential for msDNA production, is linked to the msd region, (Lim and Maas, 1989; Lampson et al., 1989 *Science*). Comparison of the msDNA systems of *M. xanthus* and *E. coli* raises an intriguing question as to how the extensive diversity found in msDNA systems has emerged in bacteria and what possible functions msDNA may have.

It is shown in U.S. Pat. No. 5,079,151 that msDNA is in fact synthesized by reverse transcriptase in a cell-free system in *M. xanthus* (Lampson et al., 1989 *Cell*).

BRIEF DESCRIPTION OF THE DRAWINGS

FIGS. 2a-2d shows a nucleotide sequence of the chromosomal region encompassing the msDNA and msdRNA coding regions and an ORF region downstream of msr.

FIG. 3 shows an amino acid sequence alignment of the msDNA-Mx162 ORF with a portion of the retroviral pol sequences from HIV and HTLV1 and ORF of msDNA-Ec67.

FIGS. 4a and 4b show a sequence similarity of the msDNA-Mx162 reverse transcriptase with other retroelements.

FIGS. 5a and 5b shows a sequence comparison of the regions around the YXDD box of various reverse transcriptases.

DETAILED DESCRIPTION OF THE INVENTION

Identification of an ORF Associated with msd

Figure 1:
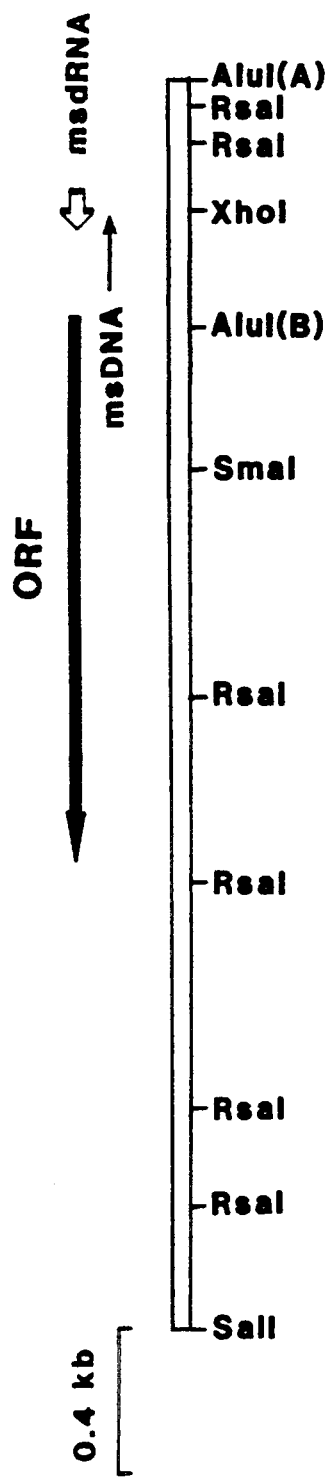
FIG. 1 shows a restriction map of the 3.4 kb fragment around msd and downstream of msr.

On the basis of mutations closely associated with msd which significantly reduce msDNA production, we assumed that in this region there is a cis- or trans-acting element which is essential for msDNA synthesis (Dhundale et al., 1988 *J. Bacteriol.*). FIG. 1 shows a restriction map around msd. The msDNA coding region is shown by a thin arrow from right to left (msd), and the msdRNA coding region by a thick open arrow (msr). In the previous work (Dhundale et al., 1988 *J. Bacteriol.*), two mutations were constructed; one, a deletion mutation in which the sequence from AluI(b) to SmaI was replaced by a gene for kanamycin resistance (see FIG. 1), and the other an insertion mutation at the SmaI site by a gene for kanamycin resistance (see FIG. 1).

In order to elucidate the properties of the element required for msDNA production, the DNA sequence of the region upstream of msd was determined as shown in FIGS. 2a–2d. A long open reading frame (ORF) beginning with an initiation codon was found 77 bases upstream of msd. The ORF is preceded by a ribosome binding sequence of AGG (residue 630 to 632) 7 bases upstream of the initiation codon. The ORF codes for a polypeptide of 485 amino acid residues. The AluI(b) and SmaI sites (see FIG. 1), where mutations inhibiting msDNA synthesis were created, are located at amino acid residue-12 and -142 of the ORF, respectively or at the nucleotide sequence from residue -672 to -675, and from residue-1061 to -1066. respectively (FIGS. 2a–2d). In FIGS. 2a–2d, msd or the DNA sequence corresponding to the msDNA sequence is indicated by the closed box on the lower strand and the orientation is from right to left. Similarly, the msdRNA sequence (msr) is also indicated by the closed box on the upper strand and the orientation is from left to right. The msd and msr regions overlap by 8 bases. An inverted repeat is also indicated by arrows with letters a1 and a2. This inverted repeat comprises a 34-base sequence immediately upstream of the branched G residue (residue 317 to 350; sequence a2 in FIGS. 2a–2d) and another 34-base sequence at the 3' end (residue 597 to 564; sequence a1). This inverted repeat is essential to form a stem structure which provides a stable secondary structure in a long primary transcript. This secondary structure is considered to serve as the primer as well as the template for msDNA synthesis (Dhundale et al., 1987; Hsu et al., 1989).

Reverse Transcriptase Required for msDNA Synthesis

From evidence presented in the accompanying paper (Inouye et al., 1989), msDNA is associated with a gene for reverse transcriptase. In both the myxobacteria and *E. coli* (Lim and Maas, 1989; Lampson et al., 1989) the chromosomal gene encoding the DNA-RNA complex is closely linked to an ORF which codes for a protein having sequence similarity to retroviral RT. This ORF has been shown to be required for the production of msDNA in both *M. xanthus* and *E. coli* and to have demonstrated RT activity in *E. coli*. Data presented in this paper further supports the predicted requirement of RT for the synthesis of msDNA as proposed by Dhundale et al. (1987).

We have described an in vitro system to produce the branched RNA-linked msDNA molecule of *M. xanthus*. This system utilizes cells rendered permeable to the uptake and incorporation of labeled nucleoside triphosphates by treatment with PEA or toluene (Halegona et al., 1976). With this system, msDNA indistinguishable from that isolated in vivo was detected. In addition, intermediate structures were identified when synthesis of DNA was disrupted with ddNTPs. The intermediate species is composed of a complex of different sized DNAs, all smaller than the full length (162 bases) DNA found in the mature molecule, associated with a strand of RNA. Each DNA molecule is linked to a different length of RNA such that together, each RNA-DNA complex is composed of the same number of residues, i.e., 239 bases. Thus, the purified intermediate species migrates as a single 239 base band, while after digestion with RNase A the intermediate appears as a ladder of various DNA bands. This intermediate structure, formed during the synthesis of msDNA, clearly demonstrates that the DNA strand is synthesized by reverse transcription from an RNA template associated with the complex. That is, as the DNA strand is extended along the RNA template, a corresponding length of RNA is digested away leaving a different sized RNA associated with each DNA in the intermediate structure. Such a concomitant ribonuclease activity associated with RT has not been demonstrated for retroviral RTs (Weiss et al., 1985). This is a clear demonstration that RNase H activity removes RNA from the 3' end, base by base, most likely in a concerted manner, as the DNA strand is extended by RT.

In U.S. Pat. No. 5,079,151, issued Jan. 7, 1992, there is described the requirement of reverse transcriptase for msDNA synthesis in vitro. There is further described the results of a gel assay to detect the in vitro production of msDNA by permeabilized cell. The msDNA synthesized in vitro is identified in comparison with an msDNA control of purified DNA after RNase treatment. To confirm that the single (240 bases) band observed prior to RNase treatment is the source of the ladder of DNA bands, this band was isolated and purified. After isolation and elution of the single msDNA band from an acrylamide gel, a portion of the purified species was treated with RNase A and then analyzed, along with an untreated sample, on a 6% acrylamide-sequencing gel. The purified msDNA band migrates as a single species of about 240–250 bases before digestion with RNase A.

In the experiment, non-viable prokaryotic cells treated with a membrane-permeabilizing agent which renders the cells permeable to nucleoside triphosphates are incubated with a reaction mixture which includes substrates required for msDNA synthesis (such as ATP, GTP, UTP and CTP) and the msDNA is isolated.

Sequence Similarity with Retroviral Reverse Transcriptases

When the amino acid sequence of the ORF was compared with known proteins, a striking similarity was found between the sequence from Leu-308 to Ser-351 and retroviral reverse transcriptases (RT). In particular, this region contains the YXDD sequence, the highly conserved sequence in all known RTs. This sequence (Tyr-344 to Asp-347) is boxed in FIGS. 2a-2d. In FIG. 3, the ORF sequence of 266 amino acid residues from Ala-170 to Lys-435 is compared with RTs from HIV (human immunodeficiency virus; Rather et al., 1986) and HTLV1 (human T-cell leukemia virus type 1; Seiki et al., 1983). As mentioned above, within the sequence of 44 amino residues from Leu-308 to Ser-351, there are 14 and 12 identical residues with HIV (32%) and HTLV1 (27%), respectively. The entire RT domains of HIV and HTLV can also be aligned with the ORF sequence from Ala-170 to Lys-435, with much less similarity as shown in FIG. 3. However, the same region was found to be extremely well aligned with the RT which was recently found in a clinical strain of *Escherichia coli* (Lampson et al., 1989 *Science*). This *E. coli* RT consists of 586 amino acid residues, and its amino terminal domain (residue-32 to -291) and the carboxyl terminal domain (residue-466 and -586) have been demonstrated to have sequence similarity with retroviral RT and ribonuclease H. This RT gene from *E. coli* was shown to be required for the production of msDNA (msDNA-Ec67) and to have reverse transcriptase activity (Lampson et al., 1989 *Science*). FIG. 3 shows that the sequence similarity between *E. coli* and *M. xanthus* RTs is distributed within almost the entire RT region; in particular in the region from Tyr-181 to Ser-212, 15 out of 32 residues are identical (47% similarity); in the region from Gly-226 to Gly-265, 19 out of 40 residues (48% similarity); in the region from Leu-308 to Ser-351, 26 out of 44 residues (59% similarity); and in the region from Lys-354 to Asn-408, 21 out of 55 residues (38% similarity). Overall, similarity from Ala-170 to-Lys-435 is 32% (85 out of 266 residues are identical). In spite of these similarities, the *M. xanthus* ORF does not have the domain, which shows apparent sequence similarity with ribonuclease H (RNase H). The RNase H domain is found to be located in the carboxyl terminal region of the same polypeptide in which the RT domain exists in the amino terminal region in the cases of the *E. coli* RT and other retroviral RTs. In the preceding paper, we have shown that there is a precise coupling between RT and RNase H activity (Lampson et al., 1989 *Cell*). Therefore, RNase H may still reside within the ORF, or RNase H may be encoded by a separate gene.

Sequence Similarity with Other Proteins

In contrast to the *E. coli* RT and other retroviral RTs, the ORF found in *M. xanthus* has a long amino terminal extra domain consisting of approximately 170 residues. Interestingly, this region shows some sequence similarities with the carboxyl terminal region associated with integration protein of Mo-MLV (Moloney murine leukemia virus; Shinnick et al. 1981) (see FIG. 4A); the sequence from Pro-18 to Leu-128 of the ORF shows 22% similarity (24 out of 111 residues) with the region from Pro-1070 to Leu-1179 of the gag-pol polyprotein of Mo-MLV. It should be noted that this region of Mo-MLV is unique for Mo-MLV integration protein and does not share sequence similarity with other retroviral endonucleases (Johnson et al., 1986). It is also interesting to notice that in Ty retrotransposon, this domain is located in front of the RT domain in contrast to the retroviral endonuclease domain (Clare and Farabaugh, 1985).

As pointed out above, the ORF does not have homology to *E. coli* or retroviral RNase H. Instead, it has a short sequence of approximately 80 residues after the RT domain. In this region, one can also find sequence similarity with a part of the gag region of HIV. As shown in FIG. 4B, the sequence from Gly-411 to Glu-485 has 22 identical amino acid residues (31% similarity) with the region from Gly-396 to Pro-461 of the gag protein of HIV (Ratner et al., 1985).

Requirement of Reverse Transcriptase

The fact that disruption of the ORF significantly reduced msDNA production in *M. xanthus* (Dhundale et al., 1988 *J. Bacteriol.*) and the fact that the ORF has sequence similarity with retroviral RTs strongly supports the previous hypothesis that RT is required for the synthesis of msDNA (Dhundale et al., 1987). Recently, we were able to demonstrate that msDNA is indeed synthesized by reverse transcriptase activity in a cell-free system (Lampson et al., 1989 *Cell*). The fact that a small amount of msDNA (3% of the wild type level) is still produced in the ORF mutants (Dhundale et al., 1988 *J. Bacteriol.*) is most likely due to another RT associated with smaller msDNA (msDNA-Mx65; previously assigned mrDNA; Dhundale et al., 1988 *J. Biol. Chem.*). In fact, an ORF has been found to be associated with the region responsible for msDNA-Mx65 production (Inouye, S. unpublished results).

At present it is unknown if the ORF is transcribed together with msdRNA from a common upstream promoter or if the ORF has its own independent promoter. Previously, we have identified a major RNA transcript of approximately 375 bases by S1 mapping (Dhundale et al., 1987). This transcript covers the region from approximately 75 bases upstream of msr (at around residue-256 in FIGS. 2a-2d) to approximately 70 bases upstream of msr (at around residue-632 in FIGS. 2a-2d). This indicates that this RNA transcript ends at the ribosome binding site (AGG, 630-632) of the ORF. It is possible that the primary RNA transcript covers not only the msr-msd region but also the entire ORF. This transcript of approximately at least 2 kilobases (kb) is then used as the mRNA for the ORF to produce RT. At the same time, the 5' untranslated region of 350 bases forms a stable secondary structure which serve as a primer and a template for msDNA synthesis as previously proposed (Dhundale et al., 1987). Because of the secondary structure, the 5' end region is probably much more stable than the ORF mRNA region. As a result, only the 375-base RNA from the 5' end of the transcript was detected in the previous work. In *E. coli*, the RT gene was shown to be transcribed from a single promoter for the msr region (Lampson et al., 1989 *Science*).

Evolution of Reverse Transcriptase

All of the RTs so far identified are from eukaryotic origins, and associated with either retroviruses or retrotransposons. DNA synthesis for retroviruses and transposition events for retrotransposons occur via RNA which is used as a template for RTs (see review by Varmus, 1985). From amino acid similarity in various RTs, possible evolutionary relationships among these RTs has been proposed (Yuki et al., 1986).

Figure 5B:
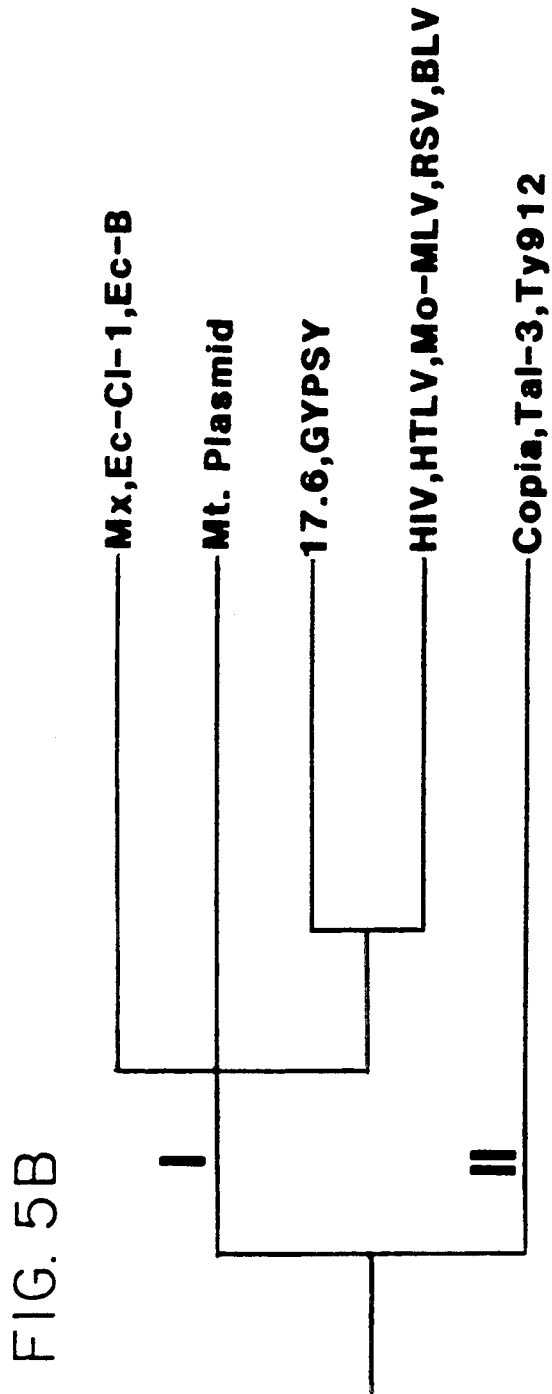

The present invention demonstrates that RTs are not specific to eukaryotes but exist in prokaryotes as well. An intriguing question arises as to the evolutionary relationship between prokaryotic and eukaryotic RTs and the origin of RT. In order to compare the amino acid sequences of these RTs, the sequence of the *M. xanthus* RT from Gly-304 to Leu-371 was chosen, since this sequence includes the YXDD box, the most conserved region among different RTs. In FIG. 5A this sequence is compared with 13 other representative RTs from bacteria, yeast, plant, mitochondrial plasmid, and animal retroviruses. Within these 14 sequences, the D-D sequence (residues-346 and -347) is completely conserved, and both G-311 and Y-344are also well conserved except for Ty-RT. Besides these residues, L-308, P-309, Q-310, S-315, P-316, L-330, S-351, and L-371 are fairly well conserved among these sequences. On the basis of the numbers of identical amino acid residues, *M. xanthus* RT has the following similarities with other RTs; 47% (32 amino acid residues) with *E. coli* Cl-1 RT, 41% (28) with *E. coli* B RT; 24% (16) with HIV, BLV, and mitochondrial plasmid RTs; 22% (15) with Mo-MLV RT; 21% (14%) with RSV, 17.6, gypsy, and Tal-3 RTs; 19% (13) with HTLV1 RT; 15% (10) with Ty912 RT; and 9% (6) with Copia RT. On the basis of the phylogenetic relationships among RTs proposed by Yuki et al. (1986), and the present data, a dendrogram of homology of various RTs may be constructed as shown in FIG. 5B. As proposed earlier (Yuki et al., 1986), modern RTs are composed of two major groups I and II. One group (group II) consists of retrotransposons found in yeast (Ty912), plant (Tal-3), and Drosophila (Copia). Bacterial RTs seem to belong to the other group (group I) together with other retrotransposons from Drosophila such as 17.6 and gypsy, mitochondrial plasmid RT, and retroviral RTs. This indicates that both prokaryotic and eukaryotic RT genes were possibly derived from a single ancestral RT gene.

Origin of the *M. xanthus* Reverse Transcriptase

In addition to the sequence similarity between the *M. xanthus* RT and RTs from retroviruses and retrotransposons, msDNA shares other interesting similarities with retroviruses and retrotransposons; msDNA (synthesis of single-stranded DNA) starts at a site 77 bases upstream of the RT gene and the orientation of DNA synthesis is opposite to the direction of translation of the RT gene. In the case of retroviruses and retrotransposons, single-stranded DNA synthesis proceeds at the 5'-end untranslated region of an RNA molecule which serves as the mRNA for RT as well (Weiss et al., 1985). The orientation of DNA synthesis is also opposite to the direction of translation of the RT gene. In the case of msDNA synthesis an RNA transcript itself serving as a template also serves as a primer by self-annealing to form a stable secondary structure (Dhundale et al., 1987), whereas in the case of retroviruses and retrotransposons tRNAs are recruited from the cell for the priming reaction. At present it is unknown if branched RNA-linked msDNA is the final product of an unknown function or if it is a stable intermediate leading other products.

Furthermore, it is of great interest whether the *M. xanthus* RT is associated with a complex such as virus-like particles such as those found for yeast Tyl element (Eichinger and Boeke, 1988). In a preliminary experiment, msDNA of *M. xanthus* exists as a complex with proteins in the cell which sediments as a 22S particle (Viswanathan, Inouye and Inouye, unpublished result). Characterization of this complex may shed light on questions concerning the relationship between msDNA and retrocomponents as well as the functions of msDNA.

At present, there is no information to support the possibility that msDNA may be a transposable element or an element associated with a provirus (or prophages). It is important to point out that the RT gene from *M. xanthus* appears to be as old as other genomic genes for the following reasons: (a) Nine independent natural isolates of *M. xanthus* from various sites (including Fiji Island and eight different sites in the United States) contained mutually hybridizable msDNA (Dhundale et al., 1985). Since under the same hybridization condition, msDNA-Mx162 did not hybridize with msDNA-Sa163(which has extensive homology in both DNA and RNA sequences with msDNA-Mx162; Dhundale et al., (1987)), the nine independent strains of *M. xanthus* are assumed to contain almost identical msDNA. (b) The codon usage of the Mx-162 RT is almost identical to those found in other *M. xanthus* genes (Table). *M. xanthus* is known to have a very high G+C content (70%; Johnson and Ordal, 1968) and as a result, all the genes so far characterized have very high G+C contents at the third positions of codons used; 85.4% for vegA (Komano et al., 1987), 85.7% for ops (Inouye et al., 1983), 87.2% for tps (Inouye et al., 1983), 88.4% for mbhA (Romeo et al., 1986), and 93.9% for sigma factor (Inouye, S., unpublished result). The average G+C contents of the third positions is calculated to be 90.0% for these genes (Table). Surprisingly, the G+C content of the third positions of the RT codons is highest among these genes (95.5%; Table).

In contrast, the *E. coli* msDNA system including the RT gene is considered to have been acquired much later in the evolution of *E. coli*. Reasons for this conclusion include: (a) Only four strains out of 89 independent clinical *E. coli* strains were found to produce msDNAs (Lampson et al., 1989 *Science*). (b) The codon usage of the *E. coli* RT is significantly different from the general codon usage of *E. coli* genes obtained from 199 *E. coli* genes (Maruyama et al., 1986). In particular, out of 62 arginine codons used in the *E. coli* RT, 40 (65%) use AGA or AGG in contrast to 2.7% for the AGA+AGG usage among all arginine codons in 199 *E. coli* genes (See Table). The AGA and AGG codons are the least used codons in *E. coli* (Maruyama et al., 1986). In addition to AGA and AGG codons, many other codons, GCC and GCG for Ala, CGU and CGC for Arg, CAG for Gln, GGC and GGA for Gly, CAC for His, AUC and AUA for Ile, UUA, CUU and CUG for Leu, UUC for Phe, CCU and CCG for Pro, UCG for Ser, ACC and ACA for Thr, and GUC for Val. (c) Although the *E. coli* msDNAs share little sequence homology, they all share the key secondary structures of a branched rG residue, a DNA-RNA hybrid at the 3' ends of the msDNA and msdRNA, and stem-and-loop structures in RNA and DNA strands (Lampson et al., 1989 *Science;* Lim and Maas, 1989).

These results clearly demonstrate distinct differences between the msDNA systems of *E. coli* and *M. xanthus*. Myxobacteria are common organisms in soil and are found all over the world regardless of climate, and considered to diverge from their nearest bacterial relatives about $2 \times 10^9$ years ago when the atmosphere became aerobic (see a review by Kaiser, 1986). Since it is reasonable to assume that the *M. xanthus* RT gene is as old as other genomic genes, the RT gene existed much before eukaryotic cells appeared ($1.5 - 0.9 \times 10^9$ years ago). The relatedness between various prokaryotic and eukaryotic RTs as shown in FIG. 5A and B strongly supports the existence of a single ancestral gene for all RTs. It is possible that such an ancestral RT gene was independently recruited into different systems such as the msDNA system, the retrotransposon system, and the retroviral system. Alternatively, the msDNA system may be a primitive ancestral system from which retrotransposons and retroviruses originated. In this regard, it is intriguing to point out other sequence similarities between the M. xanthus RT-ORF and other retroelements (see FIGS. 4a and 4b) other than RT itself as well as the similar mode of initiation of DNA synthesis by RT as discussed earlier.

At present, it is beyond speculation why the E. coli msDNA systems are so diverged in contrast to the M. xanthus msDNA system and how they were acquired into the genomes of some E. coli strains. However, it should be noted that the E. coli RTs are most related to the M. xanthus RT indicating that they were not derived from eukaryotic origins. Possible origins of retroviruses have been discussed (Temin, 1980). The recent finding of an imposon in a genetic component for a mouse gene also raises an interesting question concerning the evolution of retroelements (Stavenhagen and Robins, 1988). Further characterization of the prokaryotic RTs and the msDNA systems will provide clues to the origin of RT and other retroelements.

It is interesting to examine if the existence of RTs in prokaryotic cells increases the rate of mutations in general or if they are responsible for enhanced mutations in response to a particular environmental challenge as described by Cairns et al., (1988). There are many other intriguing questions, such as if bacterial RTs are able to produce double-stranded DNA, and if another RT is associated with the smaller msDNA [msDNA-Mx65 or mrDNA; Dhundale et al., (1988 J. Biol. Chem.)] in addition to the Mx-162 RT.

DETAILED DESCRIPTION OF THE DRAWINGS

In FIG. 1, the locations and orientation of msDNA and msdRNA are indicated by a small arrow and an open arrow, respectively. A large solid arrow represents an ORF and its orientation. The only two AluI sites (A and B) are shown and the DNA sequence between AluI (A) and AluI (B) was determined previously by Yee et al. (1984).

In FIGS. 2a-2d, the upper strand beginning at the AluI(A) site (see FIG. 1) and ending just beyond the ORF is shown. Only a part of the complementary lower strand is shown from base-301 to -600. The boxed region of the upper strand (332–408) and the boxed region of the lower strand (401–562) correspond to the sequences of msdRNA and msDNA respectively (Dhundale et al., 1987). The starting sites for DNA and RNA and the 5' to 3' orientations are indicated by open arrows. The msdRNA and msDNA regions overlap at their 3' ends by 8 bases. The circled G residue at position 351 represents the branched rG of RNA linked to the 5' end of the DNA strand in msDNA. Long solid arrows labeled a1 and a2 represent inverted repeat sequences proposed to be important in the secondary structure of the primary RNA transcript involved in the synthesis of msDNA (Dhundale et al., 1987). The ORF begins with the initiation codon at base 640. Single letter designations are given for amino acids. The YXDD amino acid sequence highly conserved among known RT proteins is boxed. Numbers on the righthand column enumerate the nucleotide bases and numbers with a * enumerate amino acids. Small vertical arrows labeled AluI and SmaI locate the AluI and SmaI restriction cleavage sites, respectively. The DNA sequence was determined by the chain termination method (Sanger et al., 1977) using synthetic oligonucleotides as primer.

In FIG. 3, amino acid sequences are compared with matching residues assigned as follows: (o) amino acid residues shared by all four proteins; (o) amino acid residues shared by msDNA-Mx162 and msDNA-Ec-67 RTs; (x) amino acid residues shared by msDNA-Mx162RT with HIV or HTLV1 RTs. Amino acid sequences showed are from residue-177 to -439 for HIV RT (Ratner et al., 1985); residue-15 to -277 for HTLV1 RT (Seiki et al., 1983); residue-32 to -291 for Ec-67 RT (Lampson et al., 1989); and residue 170 to 435 for Mx-162 RT (this work). The YXDD consensus sequence is outlined with a box.

In FIGS. 4a and 4b, portion (A) shows the sequence similarity of the region from residue-18 to -128 of the msDNA Mx162 RT (see FIGS. 2a-2d with a carboxyl terminal region of integrase of Moloney murine leukemia virus (Mo-MI.V) (residue-1070 to -1179; Shinnick et al., 1981).

In FIGS. 4a and 4b, portion (B) shows a comparison of the sequence from residue-411 to -485 of the msDNA-Mx162 RT (see FIGS. 2a-2d with the sequence from residue-396 to -461 of the gag protein of human immunodeficiency virus (HIV; Ratner et al., 1985).

In FIGS. 5a and 5b, portion (A) shows a portion of the amino acid sequences of various reverse transcriptases. The region from residue -304 to residue 371 of the msDNA-Mx162 RT (see FIGS. 2a-2d is aligned with various RTs from different sources. The identical amino acid residues with the msDNA-Mx162 RT are indicated by open circles. The YXDD sequences are boxed. The residue numbers for the amino terminal residues and for the carboxyl terminal residues are indicated by the left and the right hand sides of the sequences, respectively. Mx-162 RT from this work (FIGS. 2a-2d); Ec-67 RT from Lampson et al. (1989); Ec-86 RT from Lim and Maas (1989); HIV RT from Ratner et al. (1985); HTLV1 RT from Seiki et al. (1983); Mo-MI.V RT from Shinnick et al. (1981); RSV (Rous sarcoma virus) RT from Dickson et al. (1982); BLV (bovine leukemia virus) RT from Rice et al. (1985). Mt. plasmid (Neurospora mitochondrial plasmid) RT from Nargang et al. (1984) 17.67 Drosophila retrotransposon from Saige et al. (1984); gypsy Drosophila retrotransposon from Yuki et al. (1986); Tal-3 plant (*Arabidopsis thaliana*) retrotransposon from Voytas and Ausubel (1988); and Ty912 yeast retrotransposon from Clare and Farabaugh (1985). Small arrows in Copia, Tal-3 and Ty912 indicate positions of insertions of extra sequences of 18, 18 and 13 residues, respectively.

In FIGS. 5a and 5b, portion (B) shows the phylogenetic relationships among various RTs listed in A. The branching positions are arbitrarily illustrated.

EXPERIMENTAL PROCEDURE

DNA Manipulation and Plasmids

DNA manipulation were performed as described by Maniatis et al (1982). The plasmid isolation was as originally described by Birnboim and Dolly (1979). Plasmid pmsSB7 containing the 5 kb SalI-BamHI fragment between the SalI anhd BamHI sites of pUC9 (Vieira and Messing, 1982) was used. After the 2.2 kb SalI-SmaI fragment from pmsSB7 was subcloned between the SalI and SmaI sites of pUC9, all RsaI fragments were gel-purified and cloned into pUC9 for DNA sequencing.

DNA sequence

DNA sequence was determined by the chain termination method (Sanger et al., 1977) using single-stranded or double-stranded DNA as templates with synthetic oligonucleotides.

Other Materials and Methods

Restriction enzymes were purchased from either Bethesda Research Laboratories or New England BioLabs. [α-$^{35}$S] dATP were from Amersham. Sequenase, Version 2.0 Kit was purchased from United States Biochemical Corporation for DNA sequences.

Cyborg program from International Biotechnologies Inc. was used to search sequence homology in GenBank Release 55.

A New Designation for msDNA

The growing number of newly discovered species of msDNA, a new designation for this molecule has been adopted based on the host organism in which it is found and the size of its single-stranded DNA. For example, msDNA from *M. xanthus* is now msDNA-Mx162.

REFERENCES

Birnhoim H. C., and J. Dolly (1979). A rapid alkaline extraction procedure for screening recombinant plasmid DNA. *Nucl. Acid Res.* 7, 1513-1523.

Cairns, J., Overbaugh, J., and Miller, S. (1988). The origin of mutants. *Nature* 335, 142-145.

Clare, J., and Farabaugh, P. (1985). Nucleotide sequence of a yeast Ty element: Evidence for an unusual mechanism of gene expression. *Proc. Natl. Acad. Sci. USA* 82, 2829-2833.

Dhundale, A., Furuichi, T., Inouye, M., and Inouye, S. (1988 *J. Bacteriol.*). Mutations that affect the production of the branched RNA-linked msDNA in *Myxococcus xanthus. J. Bacteriol.* 170, 5620-5624.

Dhundale, A., Furuichi, T., Inouye, S., and Inouye, M. (1985). Distribution of multicopy single-stranded DNA among mxyobacterta and related species. *J. Bacteriol.* 164, 914-917.

Dhundale, A., Inouye, M., and Inouye, S. (1988 *J. Biol. Chem.*). A new species of multicopy single-stranded DNA from *Myxococcus xanthus* with conserved structural features. *J. Biol. Chem.*, 263, 9055-9058.

Dhundale, A., Lampson, B., Furuichi, T., Inouye, M., and Inouye, S. (1987). Structure of msDNA from *Myxococcus xanthus:* Evidence for a long, self-annealing RNA precursor for the covalently linked, branched RNA. Cell 51, 1105-1112.

Dickson, C., Eisenman, R., Fan, H., Hunter, E., and Teich, N. (1982). in Weiss, R., Teich, N., Varmus, H., and Coffin, J. (eds.) RNA Tumor Viruses, Molecular Biology of Tumor Viruses, ed. 2, Cold Spring Harbor Laboratory N.Y., pp. 513-648.

Eichinger, D. J., and Boeke, J. D. (1988), The DNA intermediate in yeast Ty1 element transposition copurifies with virus-like particles: Cell-free Ty1 transposition. *Cell,* 54, 955-966.

Furuichi, T., Dhundale, A., Inouye, M., and Inouye, S. (1987 *Cell* 48, 47-53). Branched RNA covalently linked to the 5' end of a single-stranded DNA in *Stigmatella aurantiaca:* structure of msDNA. *Cell* 48, 47-53.

Furuichi, T., Inouye, S., and Inouye, M. (1987 *Cell* 48, 55-62). Biosynthesis and structure of stable branched RNA covalently linked to the 5' end of multicopy single-stranded DNA of *Stigmatella aurantiaca. Cell* 48, 55-62.

Hsu, M. Y., Inouye, S., and Inouye, M. (1989). Structural requirements of the RNA precursor for the biosynthesis of the branched RNA-linked msDNA of *Myxococcus xanthus. J. Biol. Chem.* 264.

Inouye, S., Franceschini, T., and Inouye, M. (1983). Structural similarities between the development-specific protein S from a Gram-negative bacterium *Myxococcus xanthus. Proc. Natl. Acad. Sci. USA* 80, 6829-6833.

Johnson, J. L. and Ordal, E. J. (1968). Deoxyribonucleic acid homology in bacterial taxonomy: Effect of incubation temperature on reaction specificity. *J. Bacteriol.* 95, 893-900.

Johnson, M. S., McClure, M. A., Feng, D. -F., Gray, J., and Doolittle, R. F. (1986). Computer analysis of retroviral pol genes: Assignment of enzymatic functions to specific sequences and homologies with nonviral enzymes. *Proc. Natl. Acad. Sci. USA* 83, 7648-7652.

Kaiser, D. (1986). Control of multicellular development: Dictyostelium and Myxococcus. *Ann. Rev. Genet.* 20, 539-566.

Komano, T., Franceschini, T., and Inouye, S. (1987). Identification of a vegetative promoter in *Myxococcus xanthus. J. Mol. Biol.* 196,517-524.

Lampson, B. C., Inouye, M., and Inouye, S. (1989 *Cell*). Reverse transcriptase with concomitant ribonuclease H activity in a cell-free system for the synthesis of msDNA in *Myxococcus xanthus.* Cell 56, 701-707.

Lampson, B. C., Sun, J., Hsu, M. Y., Vallejo-Ramirez, J., Inouye, S., and Inouye, M. (1989 *Science*). Reverse transcriptase in a clinical strain of *Escherichia coli:* Its requirement for the production of branched RNA-linked msDNA. *Science,* 243, 1033-1085.

Lim, D., and Maas, W. K. (1989). A chromosomally encoded reverse transcriptase is produced in *Escherichia coli* B. *Proc. Natl. Acad. Sci. USA* in press.

Maniatis, T., Fritsch, E. F., and Sambrook, J. (1982). Molecular Cloning: A laboratory manual. Cold Spring Harbor Laboratory, Cold Spring Harbor, New York.

Maruyama, T., Gojobori, T., Aota, S., and Ikemura, T. (1986). Codon usage tabulated from the GenBank genetic sequence data. *Nuc. Acid Res.* 14, r151-r189.

Nargang, F. E., Bell, J. B., Stohl, L. L., and Lambowitz, A. M. (1984). The DNA sequence and genetic organization of Neurospora mitochondrial plasmid suggest a relationship to introns and mobile elements. *Cell* 38, 441-453.

Ratner, L., Haseltine, W., Patarca, R., Livak, K. J., Strarcich, B., Josephs, S. F., Doran, E. R., Rafalski, J. A., Whitehorn, E. A., Baumeister, K., Ivanoff, L., Petteway Jr., S. R., Pearson, M. L., Lautenberger, J. A., Papas, T. S., Ghrayeb, J., Chang, N., Gallo, R. C., and Wong-Staal, F. (1985). Complete nucleotide sequence of AIDS virus, HTLV-III. *Nature* 313, 277-283.

Rice, N. R., Stephens, R. M., Burny, A., and Gilden, R. V. (1985). The gag and pol genes of bovine leukemia virus: nucleotide sequence and analysis. *Virology* 142, 357-377.

Romeo, J. M., Esmon, B., and Zusman, D. R. (1986). Nucleotide sequence of myxobacterial hemagglutinin gene contains four homologous domains. *Proc. Natl. Acad. Sci. USA* 83, 6332-6336.

Saigo, K., Kugimiya, W., Matsuo, Y., Inouye, S., Yoshioka, K., and Yuki, S. (1984). Identification of the coding sequence for a reverse transcriptase-like enzyme in a transposable genetic element in *Drosophila melanogaster. Nature* 312, 659-661.

Sanger, F., Nicklen, S., and Coulson, A. R. (1977). DNA sequencing with chain-terminating inhibitors. *Proc. Natl. Acad. Sci. USA* 74, 5463-5467.

Seiki, M., Hattori, S., Hirayama, Y., and Yoshida, M. (1983). Human adult T-cell leukemia virus: complete nucleotide sequence of the provirus genome integrated in leukemia cell DNA. *Proc. Natl. Acad. Sci. USA* 80, 3618-3622.

Shinnick, T. M., Lerner, R. A., and Sutcliffe, J. G. (1981). Nucleotide sequence of Moloney murine leukemia virus. *Nature* 293, 543-548.

Stavenhagen, J. B., and Robins, D. M. (1988). An ancient provirus has imposed androgen regulation on the adjacent mouse sex-linked protein gene. *Cell* 55, 247-254.

Temin, H. M. (1980). Origin of retroviruses from cellular movable genetic elements. *Cell* 21, 599-600.

Varmus, H. E. (1985). Reverse transcriptase rides again. *Nature* 314, 584-585.

Vieira, J., and Messing, J. (1982). The pUC plasmids, and M13mp7-derived system for insertion mutagenesis and sequencing with synthetic universal primers. *Gene* 19, 259-268.

Voytas, D. F., and Ausubel, F. M. (1988). A copia-like transposable element family in *Arabidopsis thaliana. Nature* 336, 242-244.

Weiss, N., Teich, H., Varmus, H., Coffin, J. Eds. (1985). RNA Tumor Viruses Vol. 2 (Cold Spring Harbor Laboratory, cold Spring Harbor, N.Y.).

Yee, T., Furuichi, T., Inouye, S., and Inouye, M. (1984). Multicopy single-stranded DNA isolated from a gram-negative bacterium, *Myxococcus xanthus. Cell* 38, 203-209.

Yuki, S., Ishimaru, S., Inouye, S., and Saigo, K. (1986). Identification of genes for reverse transcriptase-like enzymes in two Drosophila retrotransposons, 412 and gypsy; rapid detection method of reverse transcriptase genes using YXDD box probes. *Nucl. Acid Res.* 14, 3017-3030.

All of the above references are explicitly incorporated herein by reference except reference Lim and Maas, bottom of page 18, top of page 19.

TABLE

Codon Usages of the *M. xanthus* and *E. coli* Reverse Transcriptases and Various *M. xanthus* Gene Products.

| | | *M. xanthus* | | | | | | | | *E. coli* | | |
| | | RT[a] | | Other Genes | | | | | | | Rt[g] | | Av[h] |
| a. a. | Codon | # | %[b] | VegA[c] # | ops[d] # | tpd[d] # | mbhA[e] # | Sigma[f] # | Total | %[b] | # | %[b] | %[b] |
|---|---|---|---|---|---|---|---|---|---|---|---|---|---|
| Ala | GCU | 4 | 5.4 | 6 | 1 | 1 | 2 | 2 | 12 | 9.3 | 15 | 55.6 | 20.2 |
| | GCG | 25 | 33.8 | 14 | 6 | 7 | 9 | 30 | 66 | 51.2 | 0 | 0 | 23.3 |
| | GCA | 2 | 2.7 | 1 | 1 | 1 | 1 | 0 | 4 | 3.1 | 9 | 33.3 | 21.6 |
| | GCG | 43 | 58.1 | 16 | 2 | 4 | 6 | 19 | 47 | 36.4 | 3 | 11.1 | 34.9 |
| Arg | CGU | 3 | 6.7 | 7 | 0 | 0 | 0 | 5 | 12 | 13.0 | 3 | 9.7 | 50.3 |
| | CGC | 25 | 55.6 | 12 | 0 | 0 | 4 | 43 | 59 | 64.1 | 1 | 3.2 | 37.9 |
| | CGA | 1 | 2.2 | 0 | 0 | 0 | 0 | 0 | 0 | 0 | 3 | 9.7 | 3.9 |
| | CGG | 15 | 33.3 | 1 | 2 | 3 | 3 | 5 | 14 | 15.2 | 4 | 12.9 | 5.1 |
| | AGA | 0 | 0 | 0 | 1 | 1 | 1 | 0 | 3 | 3.3 | 13 | 41.9 | 1.7 |
| | AGG | 1 | 2.2 | 0 | 2 | 2 | 0 | 0 | 4 | 4.3 | 7 | 22.6 | 1.0 |
| Asn | AAU | 1 | 16.7 | 1 | 1 | 2 | 1 | 1 | 6 | 7.6 | 29 | 76.3 | 32.3 |
| | AAC | 5 | 83.3 | 2 | 16 | 16 | 20 | 19 | 73 | 92.4 | 9 | 23.7 | 67.7 |
| Asp | GAU | 0 | 0 | 2 | 5 | 3 | 1 | 5 | 16 | 16.5 | 34 | 82.9 | 54.2 |
| | GAC | 24 | 100 | 10 | 7 | 7 | 11 | 46 | 81 | 83.5 | 7 | 17.1 | 45.8 |
| Cys | UGU | 0 | 0 | 0 | 0 | 0 | 0 | 0 | 0 | 0 | 8 | 72.7 | 42.1 |
| | UGC | 1 | 100 | 3 | 0 | 0 | 0 | 4 | 7 | 100 | 3 | 27.3 | 57.9 |
| Gln | CAA | 0 | 0 | 0 | 1 | 0 | 1 | 0 | 2 | 3.6 | 10 | 83.3 | 28.0 |
| | CAG | 16 | 100 | 4 | 5 | 10 | 10 | 24 | 53 | 96.4 | 2 | 16.7 | 72.0 |
| Glu | CAA | 5 | 16.7 | 1 | 3 | 2 | 1 | 13 | 20 | 15.7 | 19 | 75.1 | 71.4 |
| | GAG | 25 | 83.3 | 6 | 9 | 7 | 7 | 78 | 107 | 84.3 | 7 | 26.9 | 28.6 |
| Gly | GGU | 0 | 0 | 3 | 2 | 2 | 7 | 5 | 19 | 16.2 | 9 | 28.1 | 42.8 |
| | GGC | 28 | 90.3 | 11 | 9 | 11 | 37 | 20 | 88 | 75.2 | 4 | 12.5 | 41.1 |
| | GGA | 1 | 3.2 | 1 | 0 | 0 | 4 | 0 | 5 | 43 | 13 | 40.6 | 6.2 |
| | GGG | 2 | 6.5 | 2 | 1 | 0 | 2 | 0 | 5 | 4.3 | 6 | 18.8 | 10.0 |
| His | CAU | 0 | 0 | 0 | 0 | 0 | 1 | 0 | 1 | 14.3 | 8 | 100 | 44.3 |
| | CAC | 15 | 100 | 2 | 0 | 0 | 0 | 4 | 6 | 85.7 | 0 | 0 | 55.7 |
| Ile | AUU | 2 | 28.6 | 1 | 1 | 1 | 3 | 7 | 13 | 16.3 | 18 | 40.9 | 41.3 |
| | AUC | 5 | 71.4 | 5 | 9 | 9 | 8 | 34 | 65 | 81.3 | 7 | 15.9 | 55.1 |
| | AUA | 0 | 0 | 0 | 0 | 1 | 0 | 1 | 2 | 2.5 | 19 | 43.2 | 3.6 |
| Leu | UUA | 0 | 0 | 0 | 0 | 0 | 0 | 0 | 0 | 0 | 16 | 29.1 | 8.5 |
| | UUG | 2 | 41 | 2 | 0 | 2 | 1 | 3 | 8 | 7.3 | 15 | 27.3 | 10.1 |
| | CUU | 0 | 0 | 0 | 0 | 0 | 0 | 0 | 0 | 0 | 14 | 25.5 | 8.2 |
| | CUC | 12 | 24.5 | 3 | 1 | 1 | 9 | 23 | 37 | 33.9 | 2 | 3.6 | 9.5 |
| | CUA | 0 | 0 | 0 | 1 | 1 | 0 | 0 | 2 | 1.8 | 3 | 5.5 | 2.4 |
| | CUG | 35 | 71.4 | 7 | 10 | 8 | 4 | 33 | 62 | 56.9 | 5 | 9.1 | 61.3 |
| Lys | AAA | 0 | 0 | 1 | 2 | 2 | 1 | 0 | 6 | 5.8 | 44 | 65.7 | 76.0 |
| | AAG | 38 | 100 | 11 | 11 | 5 | 11 | 59 | 97 | 94.2 | 23 | 34.3 | 24.0 |
| Met | AUG | 3 | — | 3 | 3 | 2 | 5 | 13 | 26 | — | 11 | — | — |
| Phe | UUU | 0 | 0 | 1 | 0 | 0 | 0 | 0 | 1 | 2.9 | 28 | 87.5 | 43.7 |
| | UUC | 14 | 100 | 1 | 8 | 8 | 5 | 11 | 33 | 97.1 | 4 | 12.5 | 56.3 |

TABLE-continued

Codon Usages of the *M. xanthus* and *E. coli* Reverse Transcriptases and Various *M. xanthus* Gene Products.

| | | \multicolumn{9}{c}{*M. xanthus*} | | | \multicolumn{3}{c}{*E. coli*} |
| | | RT[a] | | \multicolumn{5}{c}{Other Genes} | | | | Rt[g] | | Av[h] |
| a.a. | Codon | # | %[b] | VegA[c] # | ops[d] # | tpd[d] # | mbhA[e] # | Sigma[f] # | Total | %[b] | # | %[b] | %[b] |
|---|---|---|---|---|---|---|---|---|---|---|---|---|---|
| Pro | CCU | 1 | 3.7 | 1 | 4 | 4 | 0 | 0 | 9 | 12.9 | 9 | 47.4 | 12.5 |
| | CCC | 10 | 37.0 | 5 | 3 | 3 | 8 | 7 | 26 | 37.1 | 1 | 5.3 | 7.4 |
| | CCA | 0 | 0 | 0 | 0 | 0 | 0 | 0 | 0 | 0 | 7 | 36.8 | 17.6 |
| | CCG | 16 | 59.3 | 7 | 4 | 5 | 3 | 16 | 35 | 50.0 | 2 | 10.5 | 62.5 |
| Ser | UCU | 1 | 3.8 | 0 | 0 | 0 | 1 | 0 | 1 | 1.3 | 11 | 31.4 | 20.5 |
| | UCC | 12 | 46.2 | 2 | 6 | 6 | 6 | 10 | 30 | 40.0 | 4 | 11.4 | 20.4 |
| | UCA | 1 | 3.8 | 0 | 0 | 0 | 0 | 0 | 0 | 0 | 9 | 25.7 | 8.9 |
| | UCG | 7 | 26.9 | 1 | 2 | 2 | 4 | 6 | 15 | 20.0 | 1 | 2.9 | 12.9 |
| | AGU | 0 | 0 | 0 | 0 | 0 | 1 | 0 | 1 | 1.3 | 5 | 14.3 | 9.8 |
| | AGC | 5 | 19.2 | 4 | 5 | 4 | 5 | 10 | 28 | 37.3 | 5 | 14.3 | 27.5 |
| Thr | ACU | 0 | 0 | 0 | 1 | 0 | 2 | 0 | 3 | 4.3 | 14 | 36.8 | 21.2 |
| | ACC | 7 | 24.1 | 2 | 7 | 7 | 14 | 12. | 42 | 60.0 | 3 | 7.9 | 48.6 |
| | ACA | 0 | 0 | 0 | 0 | 0 | 1 | 0 | 1 | 1.4 | 16 | 42.1 | 9.2 |
| | ACG | 22 | 75.9 | 2 | 1 | 1 | 8 | 12 | 24 | 34.3 | 5 | 13.2 | 21.0 |
| Trp | UGG | 9 | — | 1 | 0 | 0 | 12 | 2 | 15 | — | 0 | — | — |
| Tyr | UAU | 0 | 0 | 0 | 0 | 0 | 1 | 0 | 1 | 3.1 | 28 | 93.3 | 47.7 |
| | UAC | 3 | 100 | 3 | 6 | 6 | 7 | 9 | 31 | 96.9 | 2 | 6.7 | 52.3 |
| Val | GUU | 0 | 0 | 0 | 1 | 1 | 1 | 0 | 3 | 2.8 | 17 | 58.6 | 31.8 |
| | GUG | 7 | 18.4 | 4 | 5 | 5 | 7 | 26 | 47 | 43.5 | 0 | 0 | 17.6 |
| | GUA | 0 | 0 | 0 | 0 | 0 | 0 | 0 | 0 | 0 | 7 | 24.1 | 17.7 |
| | CUG | 31 | 81.6 | 6 | 10 | 10 | 10 | 22 | 58 | 53.7 | 5 | 17.2 | 32.9 |
| Total a.a. | | 485 | | 178 | 175 | 173 | 267 | 639 | 1432 | | 586 | | |
| G or C in the 3rd base (%) | | 95.5 | | 85.4 | 85.7 | 87.2 | 88.4 | 93.9 | 90.0 | | | | |

[a] From this work
[b] Calculated for each amino acid
[c] Komano et al. (1987)
[d] Inouye et al. (1983)
[e] Romeo et al. (1986)
[f] Inouye, S., unpublished data
[g] Lampson, B. et al. (1989b)
[h] Average from 199 *E. coli* genes (Maruyawa et al. 19

We claim:

1. An isolated bacterial reverse transcriptase having a sequence of amino acid residues as shown in FIGS. 2a–2d.

2. The isolated bacterial reverse transcriptase of claim 1 which is expressed from a cloned gene.

* * * * *

UNITED STATES PATENT AND TRADEMARK OFFICE
CERTIFICATE OF CORRECTION

PATENT NO. : 5,320,958
DATED : June 14, 1994
INVENTOR(S) : Inouye et al.

It is certified that error appears in the above-identified patent and that said Letters Patent is hereby corrected as shown below:

<u>Column 1</u>,
Line 15, before "SUMMARY OF THE INVENTION" please insert the following paragraph:
-- The U.S. Government has a paid-up license in this invention and the right in limited circumstances to require the patent owner to license others on reasonable terms as provided for by the terms of Grant Nos. GM26843 and GM44012 awarded by the NIH. --

Signed and Sealed this

Twenty-fourth Day of August, 2004

JON W. DUDAS
*Director of the United States Patent and Trademark Office*